United States Patent
Zhang et al.

(10) Patent No.: US 10,166,217 B2
(45) Date of Patent: Jan. 1, 2019

(54) FUNGAL KERATITIS PROPHYLACTIC OR THERAPEUTIC AGENT

(71) Applicant: SANTEN PHARMACEUTICAL CO., LTD., Osaka-shi (JP)

(72) Inventors: Jinzhong Zhang, Emeryville, CA (US); Masaaki Kageyama, Emeryville, CA (US)

(73) Assignee: SANTEN PHARMACEUTICAL CO., LTD., Osaka (JP)

( * ) Notice: Subject to any disclaimer, the term of this patent is extended or adjusted under 35 U.S.C. 154(b) by 0 days.

(21) Appl. No.: 15/760,210

(22) PCT Filed: Sep. 13, 2016

(86) PCT No.: PCT/JP2016/077014
§ 371 (c)(1),
(2) Date: Mar. 14, 2018

(87) PCT Pub. No.: WO2017/047597
PCT Pub. Date: Mar. 23, 2017

(65) Prior Publication Data
US 2018/0271841 A1    Sep. 27, 2018

Related U.S. Application Data

(60) Provisional application No. 62/220,847, filed on Sep. 18, 2015.

(51) Int. Cl.
| | | |
|---|---|---|
| A61K 31/436 | (2006.01) | |
| A61K 47/34 | (2017.01) | |
| A61K 9/00 | (2006.01) | |
| A61P 27/02 | (2006.01) | |
| A61K 47/10 | (2017.01) | |

(52) U.S. Cl.
CPC .......... *A61K 31/436* (2013.01); *A61K 9/0048* (2013.01); *A61K 47/10* (2013.01); *A61K 47/34* (2013.01); *A61P 27/02* (2018.01)

(58) Field of Classification Search
None
See application file for complete search history.

(56) References Cited

U.S. PATENT DOCUMENTS

2006/0182771 A1    8/2006    Dor et al.

FOREIGN PATENT DOCUMENTS

| JP | 2008-530128 A | 8/2008 |
|---|---|---|
| WO | 2006/086750 A1 | 8/2006 |
| WO | 2007/112052 A2 | 10/2007 |

OTHER PUBLICATIONS

Foldenauer et al., Journal of Immunology (2013), 190(11), pp. 5649-5658.*
Zapata et al., Ocular Immunology and Inflammation (2012), 20(5), pp. 354-359.*
Jiang et al., Investigative Ophthalmology & Visual Science (2014), 55(4). pp. 2180-2190.*
International Preliminary Report on Patentability received for PCT Patent Application No. PCT/JP2016/077014, dated Mar. 29, 2018, 11 pages (7 page of English Translation and 4 pages of Official Copy).
International Search Report and Written Opinion received for PCT Patent Application No. PCT/JP2016/077014, dated Dec. 6, 2016, 14 pages (7 pages of English Translation and 7 pages of Official Copy).
O'Day et al., "Corneal Penetration of Topical Amphotericin B and Natamycin", Current Eye Research, vol. 5, No. 11, 1986, pp. 877-882.
Prajna et al., "Comparison of Natamycin and Voriconazole for the Treatment of Fungal Keratitis", Archives of Ophthalmology, vol. 128, No. 6, 2010, pp. 672-678.
Uchiyama, "Topical Fluconazole: High Intraocular Penetration without Corneal Toxicity", Journal of the Juzen Medical Society, vol. 110, No. 5, 6, 2001, pp. 339-347. (33 pages of English Translation and 9 pages of Official Copy).
Vézina et al., "Rapamycin (AY-22,989), A New Antifungal Antibiotic. I. Taxonomy of the Producing Streptomycete and Isolation of the Active Principle", The Journal of Antibiotics, vol. 28, No. 10, 1975, pp. 721-726.
Office Action received for Vietnamese Patent Application No. 1-2018-01316, dated May 24, 2018, 2 pages (1 page of English Translation and 1 page of Official Copy).

* cited by examiner

*Primary Examiner* — Brian J Davis
(74) *Attorney, Agent, or Firm* — Morrison & Foerster LLP

(57) ABSTRACT

For preventing or treating keratomycosis, a medicament containing rapamycin or a salt thereof as an active ingredient is used.

13 Claims, 1 Drawing Sheet

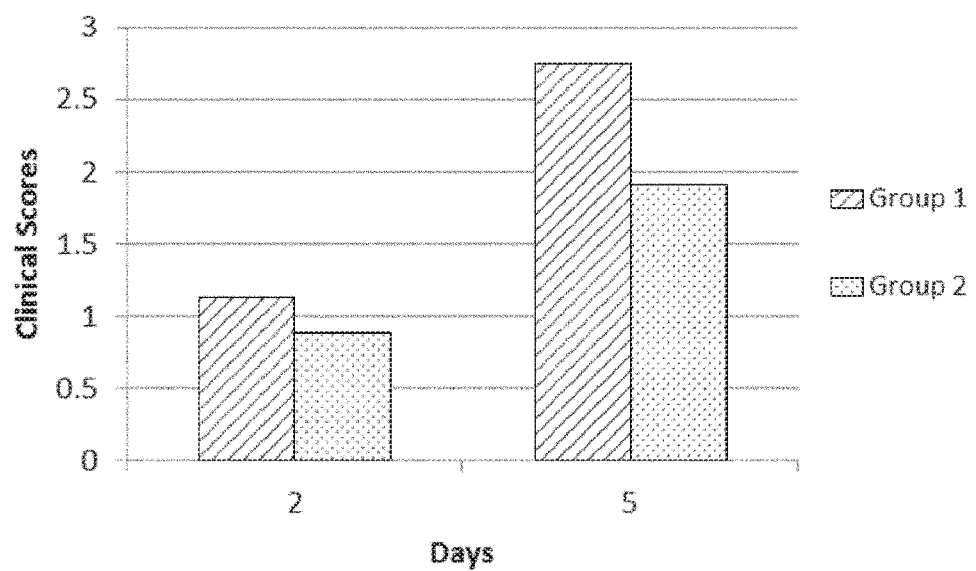

FUNGAL KERATITIS PROPHYLACTIC OR THERAPEUTIC AGENT

CROSS REFERENCE TO RELATED APPLICATIONS

This application is a U.S. National Phase patent application of International Application No. PCT/JP2016/077014, filed Sep. 13, 2016, which claims priority to U.S. Provisional Application No. 62/220,847, filed Sep. 18, 2015, the disclosures of which are incorporated herein by reference in their entirety.

TECHNICAL FIELD

The present invention relates to an agent for prevention or treatment of keratomycosis, which contains rapamycin or a salt thereof as an active ingredient.

BACKGROUND ART

Keratomycosis is an infection of the cornea induced by fungi (mold), and is also called mycotic keratitis. Keratomycosis is known to occur from an injury by a plant or the like, continuous wear of soft contact lenses, long-term use of steroid eye drops, or the like. Keratomycosis is often difficult to diagnose and, in addition, unless appropriately treated at an early stage, becomes intractable and leaves severe corneal scars, resulting in decreased vision.

A generally used ethical drug for keratomycosis is natamycin eye drops. Natamycin eye drops usually need to be administered one drop at a time and multiple times a day. Natamycin eye drops are also known to have low corneal permeability of the drug and provide insufficient therapeutic effect (Non-Patent Literature 1, Non-Patent Literature 2). On the other hand, rapamycin (also called "sirolimus") is a metabolic product of the actinomycete *Streptomyces hygroscopicus* isolated from soil of Easter Island, and was found in the 1970s as a macrolide antibiotic. Rapamycin was then found to have immunosuppressive activity, was approved in the United States and Europe as having the efficacy "prevention of organ rejection in kidney transplant patients", and has been marketed under the trade name "Rapamune (registered trademark)".

Patent Literature 1 discloses rapamycin's effect of decreasing vascular hyperpermeability.

Patent Literature 2 discloses a composition and the like for treating age-related macular degeneration (also called "AMD").

CITATION LIST

Patent Literatures

[Patent Literature 1]
Pamphlet of International Publication No. WO 2007/112052
[Patent Literature 2]
Pamphlet of International Publication No. WO 2006/086750

Non-Patent Literatures

[Non-Patent Literature 1]
Current Eye Research, 1986, November; 5(11):877-82.
[Non-Patent Literature 2]
Arch Ophthalmol, 2010, June; 128(6):672-678.

SUMMARY OF INVENTION

Technical Problem

An object to be attained by the present invention is to find a medicament for treating keratomycosis, and further find a medicament that provides a long-lasting therapeutic effect on keratomycosis with less frequent administration than existing medicaments.

Solution to Problem

The inventors studied hard in search of an agent for prevention or treatment of keratomycosis and, as a result, found that rapamycin or a salt thereof has a preventive or therapeutic effect on keratomycosis. The inventors further found that, by subconjunctivally administering an injection containing rapamycin or a salt thereof, polyethylene glycol, and ethanol, a long-lasting therapeutic effect on keratomycosis is obtained with less frequent administration than existing medicaments. In this way, the inventors accomplished the present invention.

Specifically, the present invention relates to an agent for prevention or treatment of keratomycosis, comprising rapamycin or a salt thereof as an active ingredient (this agent is hereinafter also referred to as "the agent").

The agent preferably comprises polyethylene glycol.

The concentration of the polyethylene glycol in the prevent invention is preferably 80 to 99% (w/w), more preferably 90 to 98% (w/w).

The polyethylene glycol in the present invention is preferably polyethylene glycol 400.

The agent preferably comprises ethanol.

It is preferable that an administration form of the agent is subconjunctival administration.

It is preferable that a dosage form of the agent is an injection.

The agent is preferably arranged such that: an administration form is subconjunctival administration; a dosage form is an injection; a concentration of the rapamycin or the salt thereof is 1 to 5% (w/w); and the agent comprises ethanol and polyethylene glycol 400, and a concentration of the polyethylene glycol 400 is 90 to 98% (w/w).

The agent is preferably arranged such that: an administration form is subconjunctival administration; a dosage form is an injection; the concentration of the rapamycin or the salt thereof is 2 to 4% (w/w); and the agent comprises ethanol and polyethylene glycol 400, a concentration of the ethanol is 4% (w/w), and the concentration of the polyethylene glycol 400 is 92 to 94% (w/w).

The agent is preferably adapted to be administered at an interval of at least 5 or more days.

In the present invention, it is preferable that a fungus (fungi) causing the keratomycosis is/are at least one selected from the group consisting of the genera *Candida, Fusarium, Saccharomyces, Penicillium*, and *Aspergillus*. It is preferable that a fungus of the genus *Candida* is *C. albicans*.

Another aspect of the present invention relates to a pharmaceutical composition for preventing or treating keratomycosis, comprising rapamycin or a salt thereof as an active ingredient.

A further aspect of the present invention relates to rapamycin or a salt thereof for use in prevention or treatment of keratomycosis.

Yet another aspect of the present invention relates to use of rapamycin or a salt thereof for the manufacture of a medicament for preventing or treating keratomycosis.

A yet further aspect of the present invention relates to a method for treating keratomycosis, the method comprising administering an effective amount of rapamycin or a salt thereof.

Advantageous Effects of Invention

According to the present invention, it is possible to provide an agent for prevention or treatment of keratomycosis, which contains rapamycin or a salt thereof as an active ingredient. Furthermore, by subconjunctivally administrating an injection containing rapamycin or a salt thereof, polyethylene glycol, and ethanol, a long-lasting therapeutic effect on keratomycosis can be obtained with less frequent administration than existing medicaments.

BRIEF DESCRIPTION OF DRAWINGS

The FIGURE is a graph showing the results of a test to evaluate the pharmacological effect of rapamycin on animal (rabbit) models of keratomycosis.

DESCRIPTION OF EMBODIMENTS

The following description will discuss the present invention in detail.

Rapamycin is also called sirolimus, and is a substance represented by the following structural formula.

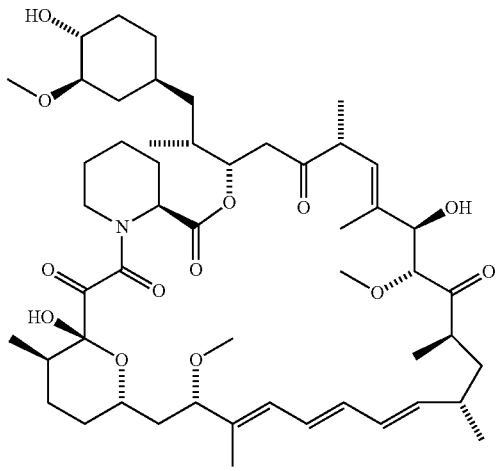 [SMILES: CO[C@H]1C[C@@H]2CC[C@@H](C)[C@@](O)(O2)C(=O)C(=O)N2CCCC[C@H]2C(=O)O[C@H]([C@H](C)C[C@@H]2CC[C@@H](O)[C@H](OC)C2)CC(=O)[C@H](C)/C=C(\C)[C@@H](O)[C@@H](OC)C(=O)[C@H](C)C[C@H](C)/C=C/C=C/C=C/1C]

A salt of rapamycin is not particularly limited, provided that it is a pharmaceutically acceptable salt. Examples include: salts of rapamycin with inorganic acids such as hydrochloric acid, hydrobromic acid, hydriodic acid, nitric acid, sulfuric acid, and phosphoric acid; salts of rapamycin with organic acids such as acetic acid, fumaric acid, maleic acid, succinic acid, citric acid, tartaric acid, adipic acid, gluconic acid, glucoheptonic acid, glucuronic acid, terephthalic acid, methanesulfonic acid, lactic acid, hippuric acid, 1,2-ethanedisulfonic acid, isethionic acid, lactobionic acid, oleic acid, pamoic acid, polygalacturonic acid, stearic acid, tannic acid, trifluoromethane sulfonic acid, benzenesulfonic acid, p-toluenesulfonic acid, lauryl ester sulfate, methyl sulfate, naphthalenesulfonic acid, and sulfosalicylic acid; quaternary ammonium salts of rapamycin with methyl bromide, methyl iodide, or the like; salts of rapamycin with halide ions such as bromide ion, chloride ion, and iodide ion; salts of rapamycin with alkali metals such as lithium, sodium, and potassium; salts of rapamycin with alkaline earth metals such as calcium and magnesium; metal salts of rapamycin with iron, zinc, or the like; salts of rapamycin with ammonia; and salts of rapamycin with organic amines such as triethylenediamine, 2-aminoethanol, 2,2-iminobis(ethanol), 1-deoxy-1-(methylamino)-2-D-sorbitol, 2-amino-2-(hydroxymethyl)-1,3-propanediol, procaine, and N,N-bis(phenylmethyl)-1,2-ethanediamine.

In a case where there are geometrical isomers or enantiomers for rapamycin or a salt thereof, those isomers or those salts are also within the scope of the present invention. In a case where there are proton tautomers for rapamycin or a salt thereof, those tautomers or those salts are also within the scope of the present invention.

Rapamycin or a salt thereof may be in the form of a hydrate or a solvate.

In a case where there are crystal polymorphs or crystal polymorph groups (crystal polymorph systems) for rapamycin or a salt thereof, those crystal polymorphs and crystal polymorph groups (crystal polymorph systems) are also within the scope of the present invention. As used herein, the crystal polymorph groups (crystal polymorph systems) mean, in a case where a crystal form changes variously depending on the conditions and states in which those crystals are, for example, produced, crystallized, or stored (it should be noted that those states also include formulated states), crystal forms at respective stages and mixtures of crystal forms in the whole process.

Rapamycin or a salt thereof can be produced in accordance with a usual method in the fields of biochemistry/organic chemistry. Alternatively, commercially-available rapamycin or a commercially-available salt can be used as rapamycin or a salt thereof.

In the present invention, the concentration of rapamycin or a salt thereof is not particularly limited, provided that rapamycin or a salt thereof is in an amount that is sufficient to achieve a desired effect. The concentration of rapamycin or a salt thereof is preferably 0.01 to 20% (w/w), more preferably 0.1 to 15% (w/w), even more preferably 0.5 to 10% (w/w), still more preferably 1 to 5% (w/w), particularly preferably 2 to 4% (w/w), most preferably 2% (w/w), 2.5% (w/w), 3% (w/w), 3.5% (w/w), or 4% (w/w).

The agent can contain polyethylene glycol. Polyethylene glycol (hereinafter also referred to as "PEG") is a polyether which is a polymer of ethylene glycol. Polyethylene glycol is represented by the structural formula $HO(CH_2CH_2O)_nH$, where n is the number of polymerized units.

In the present invention, the mean molecular weight of polyethylene glycol is preferably 100 to 2000, more preferably 100 to 1000, even more preferably 100 to 800, still more preferably 200 to 600, still more preferably 400 to 600, particularly preferably 400 or 600, most preferably 400. Specific examples of polyethylene glycol include polyethylene glycol 100 (PEG100), polyethylene glycol 200 (PEG200), polyethylene glycol 300 (PEG300), polyethylene glycol 400 (PEG400), polyethylene glycol 600 (PEG600), and polyethylene glycol 800 (PEG800).

In the present invention, the concentration of polyethylene glycol is preferably 70 to 99.99% (w/w), more preferably 80 to 99.9% (w/w), even more preferably 80 to 99% (w/w), particularly preferably 90 to 99% (w/w), most preferably 90 to 98% (w/w).

The agent can contain ethanol.

In the present invention, the concentration of ethanol is preferably 0.01 to 30% (w/w), more preferably 0.1 to 15% (w/w), even more preferably 0.5 to 10% (w/w), still more preferably 1 to 5% (w/w), particularly preferably 2 to 4% (w/w), most preferably 2% (w/w), 2.5% (w/w), 3% (w/w), 3.5% (w/w), or 4% (w/w).

In the present invention, an embodiment of the agent is, for example, an agent for prevention or treatment of keratomycosis, wherein the concentration of rapamycin or a salt thereof is 1 to 5% (w/w), and the agent contains ethanol and polyethylene glycol 400, and the concentration of polyethylene glycol 400 is 90 to 98% (w/w).

In the present invention, an embodiment of the agent is, for example, an agent for prevention or treatment of keratomycosis, wherein the concentration of rapamycin or a salt thereof is 2 to 4% (w/w), and the agent contains ethanol and polyethylene glycol 400, the concentration of ethanol is 4% (w/w), and the concentration of polyethylene glycol 400 is 92 to 94% (w/w).

In the present invention, the administration form of the agent is preferably parenteral administration, more preferably eye instillation, conjunctival sac administration, intravitreal administration, subconjunctival administration, or Tenon's capsule administration, particularly preferably subconjunctival administration.

In the present invention, the dosage form of the agent is not particularly limited, provided that the agent can be used as a pharmaceutical. Examples of the dosage form include eye drops, eye ointments, injections, and implants. The dosage form is preferably an injection, more preferably an ophthalmic injection, particularly preferably an injection for subconjunctival administration.

In a case where the agent is administered subconjunctivally, the dose is not particularly limited, provided that the dose is sufficient to achieve a desired effect. The dose is preferably 1 to 100 µL, more preferably 5 to 50 µL, even more preferably 10 to 30 µL, most preferably 10 µL, 20 µL or 30 µL, at one time. The dose of rapamycin or a salt thereof is preferably 0.001 to 30 mg/eye, more preferably 0.01 to 10 mg/eye, even more preferably 0.1 to 5 mg/eye, particularly preferably 0.2 to 1.6 mg/eye, most preferably 0.2 mg/eye, 0.3 mg/eye, 0.4 mg/eye, 0.5 mg/eye, 0.6 mg/eye, 0.7 mg/eye, 0.8 mg/eye, 0.9 mg/eye, 1 mg/eye, 1.2 mg/eye, 1.4 mg/eye or 1.6 mg/eye.

In a case where the agent is repetitively administered subconjunctivally, the dosing interval is not particularly limited, provided that it is sufficient to achieve a desired effect. The agent is administered preferably at an interval of at least once a day to once in 6 months, more preferably administered at an interval of once a day, once in 2 days, once in 3 days, once in 4 days, once in 5 days, once in 6 days, once a week, once in 2 weeks, once in 3 weeks, once a month, once in 2 months, once in 3 months, once in 4 months, once in 5 months, or once in 6 months, particularly preferably administered at an interval of at least once in 5 days, at least once a week, at least once in 2 weeks, at least once a month, or at least once in 2 months. The dosing interval can be changed appropriately, but is preferably administered at an interval of at least 5 or more days.

The agent can be prepared with the use of, depending on need, a pharmaceutically acceptable additive(s) by a generally used technique. Examples of the additives include tonicity agents, buffer agents, surfactants, and thickeners. Examples of the tonicity agents include sodium chloride. Examples of the buffer agents include sodium phosphate. Examples of the surfactants include polyoxyethylene sorbitan monooleate. Examples of the thickeners include methylcellulose.

In the present invention, a fungus causing keratomycosis is, for example, a fungus belonging to the genus *Candida, Fusarium, Saccharomyces, Penicillium, Aspergillus*, or the like. An example of a fungus of the genus *Candida* is *C. albicans*.

EXAMPLES

The following are the results of pharmacological tests and example formulations. Note, however, that these examples are given for better understanding of the present invention and not construed to limit the scope of the present invention.

[Pharmacological Test 1]

Test to evaluate pharmacological effect of rapamycin on animal (rabbit) model of keratomycosis (Preparation of Sample)

4% (w/w) rapamycin solution: This sample was prepared by dissolving rapamycin (Chunghwa Chemical Synthesis & Biotech Co., Ltd.) in a solution containing 4% (w/w) ethanol and 92% (w/w) polyethylene glycol 400.

(Test Method)

About 10 µL of a *C. albicans* solution ($1 \times 10^4$ CFU/mL to $5 \times 10^4$ CFU/mL) was administered to the central corneal stroma of the right eye of a male New Zealand white rabbit of about 3 kg, and thereby an animal (rabbit) model of keratomycosis was prepared (Cornea, Volume 26, Number 3, 336-342, April 2007).

For a base administered group (Group 1; N=4), 20 µL of a base (a solution containing 4% (w/w) ethanol and 96% (w/w) polyethylene glycol 400) was administered subconjunctivally on the day of induction.

For a rapamycin administered group (Group 2; N=4), 20 µL of a 4% (w/w) rapamycin solution (0.88 mg rapamycin) was administered subconjunctivally on the day of induction.

The right eye was observed with the use of a slit lamp on post-induction days 2 and 5, and evaluated in accordance with the McDonald-Shadduck scoring system.

(Test Results)

The FIGURE shows the results of clinical scores for each group on post-induction days 2 and 5. In the FIGURE "Group 1" indicates the base administered group, and "Group 2" indicates the rapamycin administered group.

(Consideration)

The clinical scores for the rapamycin administered group were lower than those of the base administered group on each observed day. That is, keratomycosis was found to be improved by the subconjunctival administration of rapamycin, and this showed that rapamycin is effective for prevention or treatment of keratomycosis. The results also demonstrated that, by a single subconjunctival administration of an injection containing rapamycin, polyethylene glycol, and ethanol, a remarkable therapeutic effect on keratomycosis is maintained for at least 5 days.

Example Formulations

The agent of the present invention is described more specifically with reference to example formulations. Note, however, that the present invention is not limited to these example formulations.

Example Formulation 1: Injection (4% (w/w))

In 100 g
Rapamycin: 4 g

Ethanol: 4 g
Polyethylene glycol 400: 92 g

Example Formulation 2: Injection (2% (w/w))

In 100 g
Rapamycin: 2 g
Ethanol: 4 g
Polyethylene glycol 400: 94 g

Example Formulation 3: Injection (0.2% (w/w))

In 100 g
Rapamycin: 0.2 g
Ethanol: 4 g
Polyethylene glycol 400: 95.8 g

The above injections can be prepared by dissolving rapamycin in ethanol and polyethylene glycol 400.

The present invention is not limited to the embodiments, but can be altered by a skilled person in the art within the scope of the claims. The present invention also encompasses, in its technical scope, any embodiment derived by combining technical means disclosed in differing embodiments. Further, it is possible to form a new technical feature by combining the technical means disclosed in the respective embodiments.

INDUSTRIAL APPLICABILITY

Rapamycin or a salt thereof is useful as an agent for prevention or treatment of keratomycosis.

The invention claimed is:

1. A method for prevention or treatment of keratomycosis in a subject in need thereof, comprising administering to the subject a pharmaceutical composition comprising rapamycin or a salt thereof as an active ingredient.

2. The method according to claim 1, wherein the pharmaceutical composition further comprises polyethylene glycol.

3. The method according to claim 2, wherein a concentration of the polyethylene glycol is 80 to 99% (w/w).

4. The method according to claim 2, wherein a concentration of the polyethylene glycol is 90 to 98% (w/w).

5. The method according to claim 2, wherein the polyethylene glycol is polyethylene glycol 400.

6. The method according to claim 2, wherein the pharmaceutical composition further comprises ethanol.

7. The method according to claim 1, wherein the pharmaceutical composition is administered by subconjunctival administration.

8. The method according to claim 7, wherein the subconjunctival administration is by injection.

9. The method according to claim 1, wherein the pharmaceutical composition:
is administered by subconjunctival injection;
the rapamycin or the salt thereof is present in the pharmaceutical composition at a concentration of 1 to 5% (w/w); and
the pharmaceutical composition further comprises ethanol and polyethylene glycol 400, and the polyethylene glycol 400 is present in the pharmaceutical composition at a concentration of 90 to 98% (w/w).

10. The method according to claim 9, wherein:
the concentration of the rapamycin or the salt thereof is 2 to 4% (w/w);
the ethanol is present in the pharmaceutical composition at a concentration of 4% (w/w); and
the concentration of the polyethylene glycol 400 is 92 to 94% (w/w).

11. The method according to claim 1, wherein the pharmaceutical composition is administered at an interval of at least 5 or more days.

12. The method according to claim 1, wherein a fungus (fungi) causing the keratomycosis is/are at least one selected from the group consisting of the genera *Candida, Fusarium, Saccharomyces, Penicillium*, and *Aspergillus*.

13. The method according to claim 12, wherein the fungus causing the keratomycosis comprises *C. albicans*.

* * * * *